(12) United States Patent
Coffey et al.

(10) Patent No.: US 10,864,115 B2
(45) Date of Patent: Dec. 15, 2020

(54) WOUND DRESSING MATERIALS AND METHODS OF MAKING THEREOF

(71) Applicant: Medline Industries, Inc., Northfield, IL (US)

(72) Inventors: Martin Coffey, Buffalo Grove, IL (US); Ramon Verduzco, Mundelein, IL (US)

(73) Assignee: Medline Industries, Inc., Northfield, IL (US)

( * ) Notice: Subject to any disclaimer, the term of this patent is extended or adjusted under 35 U.S.C. 154(b) by 357 days.

(21) Appl. No.: 15/970,152

(22) Filed: May 3, 2018

(65) Prior Publication Data

US 2018/0256404 A1    Sep. 13, 2018

Related U.S. Application Data

(63) Continuation of application No. 14/863,491, filed on Sep. 24, 2015, now Pat. No. 10,045,885.

(51) Int. Cl.
| | |
|---|---|
| *A61F 13/00* | (2006.01) |
| *A61L 15/18* | (2006.01) |
| *A61L 15/46* | (2006.01) |
| *A61L 15/26* | (2006.01) |

(52) U.S. Cl.
CPC .. *A61F 13/00063* (2013.01); *A61F 13/00991* (2013.01); *A61L 15/18* (2013.01); *A61L 15/26* (2013.01); *A61L 15/46* (2013.01); *A61L 2300/102* (2013.01)

(58) Field of Classification Search
None
See application file for complete search history.

(56) References Cited

U.S. PATENT DOCUMENTS

| | | | | |
|---|---|---|---|---|
| 4,480,000 | A * | 10/1984 | Watanabe | A61F 13/51498 428/76 |
| 5,122,407 | A * | 6/1992 | Yeo | A61F 13/512 428/138 |
| 5,176,918 | A * | 1/1993 | Jones | A61K 9/0014 424/449 |
| 2007/0100269 | A1* | 5/2007 | Addison | A61F 13/0203 602/48 |
| 2013/0189339 | A1* | 7/2013 | Vachon | A61K 33/38 424/404 |
| 2015/0273104 | A1* | 10/2015 | Nisbet | A61L 15/44 602/48 |
| 2015/0328053 | A1* | 11/2015 | MacPhee | A61F 13/00063 602/48 |
| 2017/0087027 | A1* | 3/2017 | Coffey | A61L 15/46 |

* cited by examiner

*Primary Examiner* — Kim M Lewis
(74) *Attorney, Agent, or Firm* — Fitch, Even, Tabin & Flannery, L.L.P.

(57) ABSTRACT

Disclosed is a wound dressing material comprising a substrate, about 2.5% to about 8% by weight of a bicarbonate, and a film-forming agent, the film-forming agent serving as a binder for said bicarbonate to said substrate, the film-forming agent and the bicarbonate being present in a ratio of between 1:2 and 2:1 with respect to one another. Also disclosed are a method for preparing a wound dressing material and a method for treating a wound.

20 Claims, 2 Drawing Sheets

WOUND DRESSING MATERIALS AND METHODS OF MAKING THEREOF

CROSS-REFERENCE TO RELATED APPLICATION

This application is a continuation of U.S. application Ser. No. 14/863,491, filed on Sep. 24, 2015, the entire content of which is incorporated herein by reference.

FIELD

The disclosure relates generally to wound dressing materials, and in some embodiments to methods of making a wound dressing material.

BACKGROUND

Many wounds, whether caused by trauma or resulting from surgical procedures, develop an odor over time. This odor is produced in connection with tissue death and the associated build-up of anaerobic bacteria at the wound site. Wound dressings and bandages can contain sodium bicarbonate to control odor emanating from a wound. The effectiveness of wound dressings and bandages to control odors generally correlates to the amount of sodium bicarbonate present in the wound dressings or bandages. Sodium bicarbonate is a powder and does not naturally adhere to cotton fibers or conventional non-woven wound dressing materials. For this reason, typically sodium bicarbonate is applied to the wound dressing or bandage as an aqueous solution and the dressing or bandage is then dried.

Sodium bicarbonate can be incorporated into a wound dressing only in limited concentrations, up to 2% w/w. At levels above 2%, it has been found that sodium bicarbonate crystallizes and that the adherence to the wound dressing becomes so weak that the sodium bicarbonate tends to fall off the dressing as a powder.

FIGURES

DETAILED DESCRIPTION

Generally, it has been found that a wound dressings may include an odor control agent, typically sodium bicarbonate, and a film forming agent. Via the use of a film-forming agent, it is possible to prepare a wound dressing that contains about 2.5% to about 8% by weight of a bicarbonate. This measurement is based on the weight of the bicarbonate molecule to the total weight of the substrate including the bicarbonate, but excluding the film-forming material and other functional additives, and excluding any other layers of a roll material or bandage or the like. The wound dressing thus prepared and advantageously provides increased odor mitigation. It has been found that about 4% bicarbonate in the substrate is a currently preferred bicarbonate loading level. At loading levels of greater than about 8%, it is believed that the product may become stiff and that the pores of the substrate may become clogged.

Figure 2:
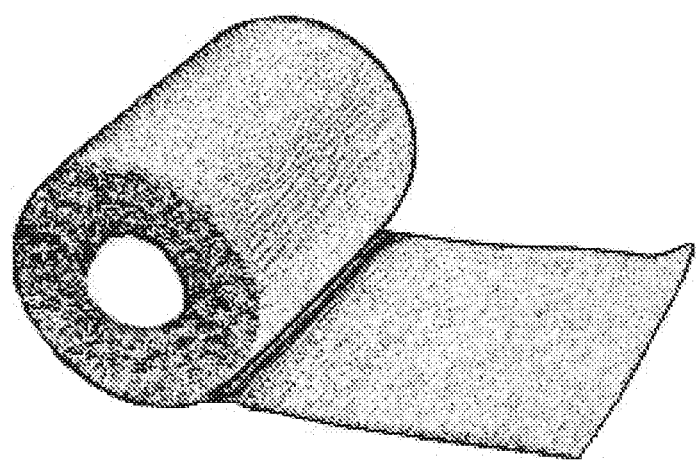
FIG. 2 is a perspective view of a roll of wound dressing material prepared in accordance with one embodiment of the invention.
Figure 3:
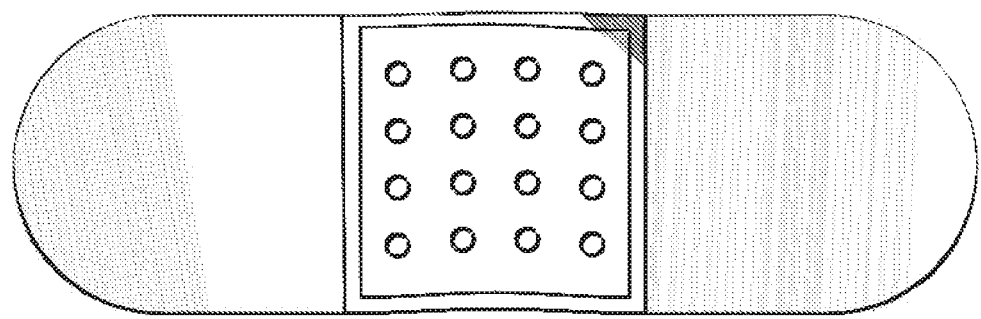
FIG. 3 is a plan view of an adhesive bandage containing wound dressing material prepared in accordance with another embodiment of the invention.

The wound dressing may take the form of a gauze, bandage pad, or the like. In some embodiments, the wound dressing may be formed as a composite material including one or more layers. For example, the wound dressing may be formed as a roll material including one layer (e.g., a single absorbent layer of wound dressing material), as shown in FIG. 2. Alternatively, the wound dressing may be formed as a roll that includes two layers (e.g., an absorbent layer of wound dressing material and a non-absorbent layer), three layers (e.g., an absorbent layer of wound dressing material, a non-absorbent layer, and an intermediate adhesive layer), or more than three layers. Instead of being formed as a roll material, the wound dressing may be in the form an individual unit having a discrete segment of absorbent wound dressing material and an adhesive backing, as shown in FIG. 3.

The wound dressing should be flexible to permit the wound dressing to conform to natural curvature of human limbs or torso and the flexibility of human skin. Generally, the wound dressing material includes a substrate that can absorb blood or other bodily fluids exuded from a wound. The substrate may for example be composed a cellulosic material, such as cotton, optionally in combination with a polymer such as polyester fiber, or may comprise polyester, rayon, or blends of the foregoing. The substrate can be a woven material such as a mesh, a non-woven material, or may take other suitable form.

In the embodiments where the wound dressing material includes a non-absorbent layer, the non-absorbent layer may be a backing layer and may be formed from materials including but not limited to polyurethane film, polyethylene film, polypropylene film, polyester, combinations thereof, or the like. In some embodiments, the non-absorbent layer may be liquid impermeable and made of a breathable material. In the embodiments where the wound dressing material includes an adhesive layer, the adhesive layer may be formed from materials including but not limited to silicone, polyurethane, or acrylic, combinations thereof, or the like. The adhesive layer permits the wound dressing to be detachably attached to the skin surrounding a wound caused by trauma, surgery, or medical condition. It will be appreciated that the inclusion of an adhesive layer in the wound dressing material is optional, and that the wound dressing material may be attached to the skin of a person using a separate wrapping or adhesive tape.

In some embodiments, the wound dressing may include a cover layer that can be removed from the wound dressing prior to use. For example, in embodiments where the wound dressing includes one or more adhesive portions that permit attachment of the wound dressing to the skin, the cover layer may overlay the adhesive portions of the wound dressing, and the adhesive portions of the wound dressing may be exposed upon detachment of the cover layer by a user from the wound dressing. The cover layer may be formed from materials including but not limited to laminated paper polyethylene, or the like.

The odor control agent is generally sodium bicarbonate, but it is contemplated that other bicarbonates may be employed. In some embodiments a portion of the bicarbonate is replaced with activated carbon. Without wishing to be limited by theory, sodium bicarbonate is believed to interact with short-chain carboxylic acids found in odiferous compounds exuded from a patient's wound or resulting from bacterial action thereon.

To increase the adherence of the bicarbonate to the substrate, a film-forming agent is used. The film-forming agent is a water-soluble material that, after being applied to a wound dressing material in aqueous form (e.g., by dipping the wound dressing material into a wound dressing solution as discussed below) and drying, can cause the bicarbonate to adhere to the wound dressing material. In some embodiments, the film forming agent can be one or more of polysaccharides, chitosan, povidone, gelatin, polyethylene glycol having a molecular weight from about 600 to about 10,000, hydroxyethylcellulose (HEC), hydroxypropylcellulose (HPC), hydroxypropylmethylcellulose (hypromellose or HPMC), hypromellose acetate succinate, polymethacrylates, poly(methyl vinyl ether/maleic anhydride) having an average molecular weight of about 200,000 to about 2,000,000, shellac, and combinations thereof. The polyethylene glycol may have a molecular weight from about 1,000 to about 8,000 in one approach, from about 2,000 to about 6,000 in another approach, from about 3,000 to about 4,000 in yet another approach, and from about 3,300 to about 3,400 in still another approach. Polysaccharides suitable for use as a film forming agent may include, but are not limited to alginate salts, carrageenan, xanthan gum, guar gum, or the like.

Generally, the bicarbonate and film-forming agent are dissolved in aqueous solution and introduced to the substrate via spraying or dipping. The bicarbonate or other odor control agent and the film-forming agent may be present in the aqueous solution in any suitable amounts. For example, the bicarbonate may be present in the solution in amounts of from about 1% to about 10% w/w % (based on the total weight of the solution) and the film-forming agent in amounts ranging from about 0.5% to about 16% w/w %. In some cases, the amount of bicarbonate in the solution may be from about 2% to about 9%; in another embodiment, from about 3% to about 8%; in another embodiment, from about 4% to about 7%; and in another embodiment from about 5% to about 6% w/w %. The film-forming agent may be present in amounts ranging from about 1% to about 12%; in other embodiments, from about 2% to about 8%; and in other embodiments, from about 3% to about 7%. The balance may be water.

In many embodiments, the bicarbonate or other odor control agent and the film forming agent may be present in the aqueous solution in a ratio of from 1:2 to about 2:1 relative to each other. In one embodiment, this ratio is a 1:1 ratio. For instance, the solution may comprise 4% by weight sodium bicarbonate, 4% by weight film-forming agent, and 92% water.

Some of the film forming agents, when used in the wound dressing solution together with an odor control agent (e.g., sodium bicarbonate), may increase the stiffness of the wound dressing material. To alleviate possible irritation and/or discomfort at the wound site as a result of application of a wound dressing material having a high degree of stiffness to a wound, in some embodiments, the wound dressing solution may include one or more plasticizers in addition to the odor control agent and the film forming agent. Any suitable plasticizer may be employed, and when employed, the plasticizer may be present in any suitable amount. Plasticizers suitable for use in wound dressings and wound dressing solutions as described herein include glycerin, polyethylene glycols with molecular weight up to about 600, and combinations thereof, or the like. It will be appreciated that certain of the heretofore described film-forming materials, such as polyethylene glycol (PEG) with molecular weight ranging from about 1,000 to about 10,000, may themselves act to some extent as plasticizers such that no additional plasticizer is necessary.

In addition to bicarbonate, it is contemplated in some embodiments that the wound dressing material can be impregnated with various other functional ingredients. For instance, in some embodiments, the wound dressing solution may include from about 0.1% to about 1% w/w % of a buffer, for example, a citrate buffer or the like. If a buffer is employed, it is contemplated that a desired pH range for the buffered material would be in the range of about 6.8-7.5. Lower amounts of buffer would correlate to lower amounts of bicarbonate in the wound dressing and higher amounts of buffer would be used when higher amounts of bicarbonate are used.

The wound dressing solution may include from about 5-5000 ppm of an antimicrobial material, for example colloidal silver. The wound dressing can be, for example, a silver antimicrobial wound dressing, a silver antimicrobial barrier wound dressing, a non-adhesive foam wound dressing, an adhesive foam wound dressing, and/or combinations thereof, etc. The wound care products can include any hydrogel, hydrogel with silver, hydrogel filler with silver, hydrogel sheet, hydrogel sheet with silver, hydrogel perforated sheet with silver, hydrogel barrier with silver, tape, transparent film, wound filler, foam, foam with silver, combinations thereof, etc. For example, the wound care products can be products known as DERMA-GEL, TENDERWET, SILVASORB, AQUAFLO, AQUASORB, CARRADRESS CLEAR, CLEARSITE, or CURAGEL, products available from Medline Industries, Inc. If benzalkonium chloride is used as an antimicrobial agent, then a typical range would be about 1000-1300 ppm. If PHMB is used, the typical range of use is about 2000-5000 ppm.

It is contemplated that the substrate may incorporate other materials, such as one or more superabsorbent polymers. Additionally, in some embodiments, the dressing solution may include from about 0.01% to about 0.5% w/w % of a nutritional or nurturing component, for example an herbal-based skin moisturizer, cleaner, or protectant. For instance, the wound dressing may be formulated using Medline's PHYTOPLEX formulations, which are composed of botanical extracts and blue-green algae.

After a solution of film-forming agent and odor control agent is formed, it is applied to the substrate. In one embodiment, the odor control agent (e.g., sodium bicarbonate) and film forming agent (e.g., PEG) are added to water to provide a dipping solution. The odor control agent and the film forming agent may each be added to the liquid while in powder or liquid form. After the addition of the odor control agent and the film forming agent to the liquid, the ingredients may be stirred until the odor control agent and the film forming agent fully dissolve in the water. A plasticizer and other optional ingredients may be added.

After the wound dressing dipping solution is prepared, a wound dressing material as described above may then be dipped into the wound dressing dipping solution to apply the wound dressing dipping solution to the wound dressing material. It will be appreciated that the wound dressing dipping solution may be applied to the wound dressing material by techniques other than dipping; for example, the wound dressing dipping solution may be sprayed onto the wound dressing material through a pressurized nozzle or poured onto the wound dressing material through a spout.

After the application of the wound dressing dipping solution to the wound dressing material, the wet wound dressing material is dried. Optionally, the wound dressing material soaked with the wound dressing solution may be pressed to remove excess wound dressing dipping solution prior to drying. The wound dressing material may be vacuum-dried or air-dried at room temperature, or at an elevated temperature. Upon drying, the wound dressing dipping solution is absorbed and incorporated into the wound dressing material such that the wound dressing material is impregnated with the odor control agent and the film forming agent. Generally, the dried wound dressing material should be sterilized, for instance, using ethylene oxide as is known in the art. The sterilized wound dressing material then may be packaged as is conventional. Typical packaging is composed of a hermetically sealed packages with an optional tamper-evident feature.

The exemplary embodiments of the wound dressing materials described herein may be applied to wounds (resulting from trauma and/or surgical procedures) as well as to body areas susceptible to malodor (e.g., in association with certain medical conditions, such as adult incontinence or the like) to advantageously control and reduce the level of malodor emanating from the wound or body area. The wound dressings can be used to treat chronic wounds such as pressure sores, diabetic foot ulcers, arterial ulcers, etc.

As discussed above, the wound dressing material may take any suitable form, such as roll or patch, and may be used in any suitable application, such as adhesive bandages, nonstick/non adhesive pads, cotton rolls, sponges, and so forth.

The following non-limiting examples are provided for illustration.

Example 1

A wound dressing solution was prepared by adding 4 grams of polyethylene glycol (molecular weight 3,350) and 4 grams of sodium bicarbonate to 92 ml water and stirring the mixture in order to dissolve the polyethylene glycol and the sodium bicarbonate in the water to provide a wound dressing dipping solution including 4% w/w % polyethylene glycol, 4% w/w % sodium bicarbonate, and 92% w/w % water. Wound dressing material was then continuously introduced (i.e., dipped) into the wound dressing dipping solution to soak the wound dressing material with the wound dressing solution. The soaked wound dressing material was then pressed to eliminate some of excess wound dressing dipping solution and then dried using a hot air drier. After the wound dressing material was dried, the dried wound dressing material was sterilized with ethylene oxide and packaged as a roll material for use.

Example 2

Acetic acid is known as a short chain carboxylic acid including the same functional unit as many of the odoriferous compounds contained in bacterial by-products and body odors. As such, the ability of substrates to neutralize acetic acid can roughly be equated with their ability to eliminate odors caused by short chain fatty acids and other similar compounds. In this example, acetic acid was used as a model compound to test the efficacy of odor reduction by sodium bicarbonate in the wound dressing material.

An odor reduction screening was performed on some wound dressing materials obtained according to Example 1. Wound dressing materials were designated as "sealed" or "unsealed," the sealed dressings containing 4% PEG 3350. The wound dressing materials used in the screening were non-woven substrates treated with 0% sodium bicarbonate (sealed and unsealed), 2% sodium bicarbonate (unsealed), 4% sodium bicarbonate (sealed), and 6% sodium bicarbonate (sealed) to determine whether increasing amounts of sodium bicarbonate in the wound dressing material provide corresponding increases in wound odor reduction.

Glacial acetic acid was diluted to 1M and 0.5 mL of 1M acetic acid solution was applied via an autopipette to a 1"×2" strip of wound dressing material. The strips were placed inside 8 ounce glass jars having a lid including pre-drilled holes to allow for sensory evaluation. The samples were then allowed to sit in the glass jars for 60 minutes before being evaluated by a sensory panel.

Figure 1:
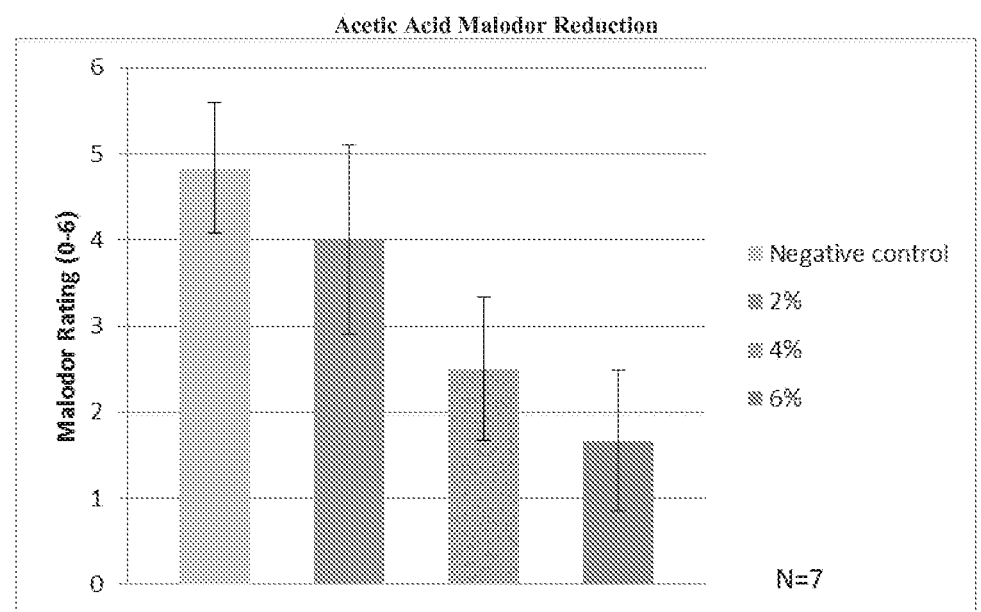
FIG. 1 is a table that represents malodor rating vs bicarbonate loading in an evaluated wound dressing material.

The unsealed 0% sodium bicarbonate wound dressing material was used as the reference sample, and was assigned a rating of 6 on a 0-6 scale. The sealed 0% sodium bicarbonate wound dressing material was included as a negative control. All wound dressing materials were then presented to the panel for evaluation. The panelists were asked to rate the level of malodor on a 0-6, with 0 representing no detectable malodor, and 6 being equivalent to the reference sample. The values for each sample were then averaged and are shown in FIG. 1. The results of the sensory evaluation depicted in FIG. 1 demonstrate that higher levels of sodium bicarbonate correspond to lower perceived malodor level.

It is thus seen that a wound dressing with an odor-control agent may be provided and used in accordance with the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A wound dressing material comprising a substrate, about 2.5% to about 8% by weight of a bicarbonate, and a film-forming agent, said film-forming agent serving as a binder for said bicarbonate to said substrate, the film-forming agent and the bicarbonate being present in a ratio of between 1:2 and 2:1 with respect to one another.

2. The wound dressing material according to claim 1, said bicarbonate comprising sodium bicarbonate.

3. The wound dressing material of claim 2, said substrate comprising a cellulosic material.

4. The wound dressing material of claim 3, said substrate further comprising a polyester.

5. The wound dressing material of claim 1, wherein the film-forming agent comprises a polysaccharide, chitosan, povidone, gelatin, a polyethylene glycol, hydroxyethylcellulose, hypromellose, a polymethacrylate, poly(methyl vinyl ether/maleic anhydride), shellac, or combinations thereof.

6. The wound dressing material of claim 1, wherein the film-forming agent comprises a polyethylene glycol having a molecular weight of about 1,000 to about 10,000.

7. The wound dressing material of claim 1, further including a plasticizer.

8. The wound dressing material of claim 7, wherein the plasticizer comprises glycerin.

9. The wound dressing material of claim 1, wherein the wound dressing material further includes at least one of a buffering agent, antimicrobial agent, and a nutritive agent.

10. The wound dressing material of claim 1 further comprising activated carbon.

11. A method of treating a wound, comprising applying a wound dressing material to a wound, said wound dressing material comprising a substrate, about 2.5% to about 8% by weight of a bicarbonate, and a film-forming agent, said film-forming agent serving as a binder for said bicarbonate to said substrate, the film-forming agent and the bicarbonate being present in a ratio of between 1:2 and 2:1 with respect to one another.

12. The method according to claim 11, said bicarbonate comprising sodium bicarbonate.

13. The method according to claim 12, said substrate comprising a cellulosic material.

14. The method according to claim 13, said substrate further comprising a polyester.

15. The method according to claim 11, wherein the film-forming agent comprises a polysaccharide, chitosan, povidone, gelatin, a polyethylene glycol, hydroxyethylcellulose, hypromellose, a polymethacrylate, poly(methyl vinyl ether/maleic anhydride), shellac, or combinations thereof.

16. The method according to claim 11, wherein the film-forming agent comprises a polyethylene glycol having a molecular weight of about 1,000 to about 10,000.

17. The method according to claim 11, further including a plasticizer.

18. The method according to claim 17, wherein the plasticizer comprises glycerin.

19. The method according to claim 11, wherein the wound dressing material further includes at least one of a buffering agent, anti-microbial agent, and a nutritive agent.

20. The method according to claim 11, wherein the wound dressing material further comprises activated carbon.

* * * * *